United States Patent [19]

Economou

[11] Patent Number: 4,943,732

[45] Date of Patent: Jul. 24, 1990

[54] METHOD AND APPARATUS FOR DEFECT DETECTION AND LOCATION

[75] Inventor: Nicholas P. Economou, Lexington, Mass.

[73] Assignee: Micrion Corporation, Peabody, Mass.

[21] Appl. No.: 394,674

[22] Filed: Aug. 16, 1989

[51] Int. Cl.$^5$ ............................................. G01N 21/88
[52] U.S. Cl. ...................................... 250/572; 250/563
[58] Field of Search ............... 250/562, 563, 571, 572; 356/237, 429–431

[56] References Cited

U.S. PATENT DOCUMENTS 4,417,149  11/1983  Takeuchi et al. .................... 250/563
4,851,696  7/1989  West .................................... 356/237

Primary Examiner—David C. Nelms
Assistant Examiner—K. Shami
Attorney, Agent, or Firm—Lahive & Cockfield

[57] ABSTRACT

Methods and apparatus for locating defects in liquid crystal display (LCD) panels include scanning the panel with a laser, detecting reflected, refracted, scattered or transmitted light, and processing signals representative of the detected light utilizing a digital processor, to detect discontinuities in the arrays of LCD elements on the panel.

22 Claims, 2 Drawing Sheets

SYSTEM BLOCK DIAGRAM

METHOD AND APPARATUS FOR DEFECT DETECTION AND LOCATION

BACKGROUND OF THE INVENTION

This invention relates generally to inspection of electronic components, and, more particularly, relates to methods and apparatus for real-time optical inspection of, and location of defects in, liquid crystal display (LCD) panels.

LCD devices are extensively utilized in a broad spectrum of applications, including computer monitors, digital instruments, calculators, watches, and aircraft and automotive displays. Quality and cost control during fabrication of such devices requires rapid and reliable inspection. Many conventional techniques for inspection of semiconductor devices share the deficiencies of limited operating speed and reliability, and high cost and complexity.

Certain conventional optical inspection systems, such as optical linewidth measurement tools, enable precise evaluation of workpiece features, utilizing a laser light beam to scan the workpiece. However, these systems do not automatically detect and locate defects in LCD devices in real-time, and do not provide integrated, interactive control of the inspection process.

It is accordingly an object of the invention to provide laser-based photometric methods and apparatus for real-time detection and location of defects in LCD devices.

It is another object of the invention to provide such methods and apparatus which operate with enhanced reliability and precision, and which provide integrated, interactiveprocess control.

Other general and specific objects of the invention will in part be obvious and will in part appear hereinafter.

SUMMARY OF THE INVENTION

The foregoing objects are attained by the invention, which provides methods and apparatus for locating defects in a liquid crystal display (LCD) panel. One aspect of the invention includes a light source for generating an interrogating light beam to impinge upon the LCD panel, scanning elements for introducing relative motion between the interrogating light beam and the LCD panel to scan the interrogating light beam in a predetermined pattern about the LCD panel, and photodetectors for detecting reflected, refracted, scattered or transmitted light resulting from impingement of the interrogating light beam upon the LCD panel.

In particular, the photodetectors generate a detector signal having an instantaneous value representative of the detected magnitude of the reflected, refracted, scattered or transmitted light. A defect detector then detects discontinuities in the value of the detector signal, representative of defects in the LCD panel.

The invention also includes position signalling elements for generating a position signal representative of the instantaneous position of the interrogating light beam with respect to the LCD panel. A location module, responsive to the detector signal and the position signal, correlates each discontinuity in the value of the detector signal with a corresponding location on the LCD panel, to assign a location to each detected defect on the LCD panel.

The light source can be a laser, and a vacuum chuck can be utilized for retaining the LCD panel in a selected position with respect to the light source. Movement of either the light source or the vacuum chuck can be actuated by beam steering elements or an X-Y stage, respectively, to provide scanning of the beam over the LCD panel.

In a further aspect of the invention, the defect detector and location module collectively include a digital processor, such as a computer or microprocessor. At least a first photodetector can be positioned to detect reflected light resulting from impingement of the interrogating light beam upon the LCD panel, and at least a second photodetector can be positioned to detect transmitted, scattered or refracted light. The digital processor asserts control signals to cause scanning of the entire LCD panel by one or more detectors, and compares the detector signals generated by the detectors to detect defects in the LCD panel.

In accordance with the invention, the digital processor can direct the scanning operation along selected paths defined by arrays of LCD elements on the LCD panel. In a typical LCD panel, these paths can take the form of a jagged square wave. Alternatively, the digital processor can direct the scanning elements to first scan along selected paths to accumulate a knowledge base corresponding to features of the LCD panel, and subsequently scan the LCD panel to detect defects therein.

The invention also comprises one or more cameras, in electrical communication with the digital processor, for generating an image of the LCD panel, and a monitor for displaying the image. The displayed image can be controlled by the digital processor to highlight the location of a detected LCD panel defect.

The invention can include a keyboard or other user input device, for controlling the operation of the digital processor; a process controller, under the direction of the digital processor, for controlling the scanning elements; and transport elements, under the direction of the digital processor, for automatic loading and unloading of LCD panels on and off the mounting elements.

The invention will next be described in connection with certain illustrated embodiments; however, it should be clear to those skilled in the art that various modifications, additions and subtractions can be made without departing from the spirit and scope of the claims.

BRIEF DESCRIPTION OF THE DRAWINGS

For a fuller understanding of the nature and objects of the invention, reference should be made to the following detailed description and the accompanying drawings, in which.

DESCRIPTION OF PREFERRED EMBODIMENTS

Figure 1:
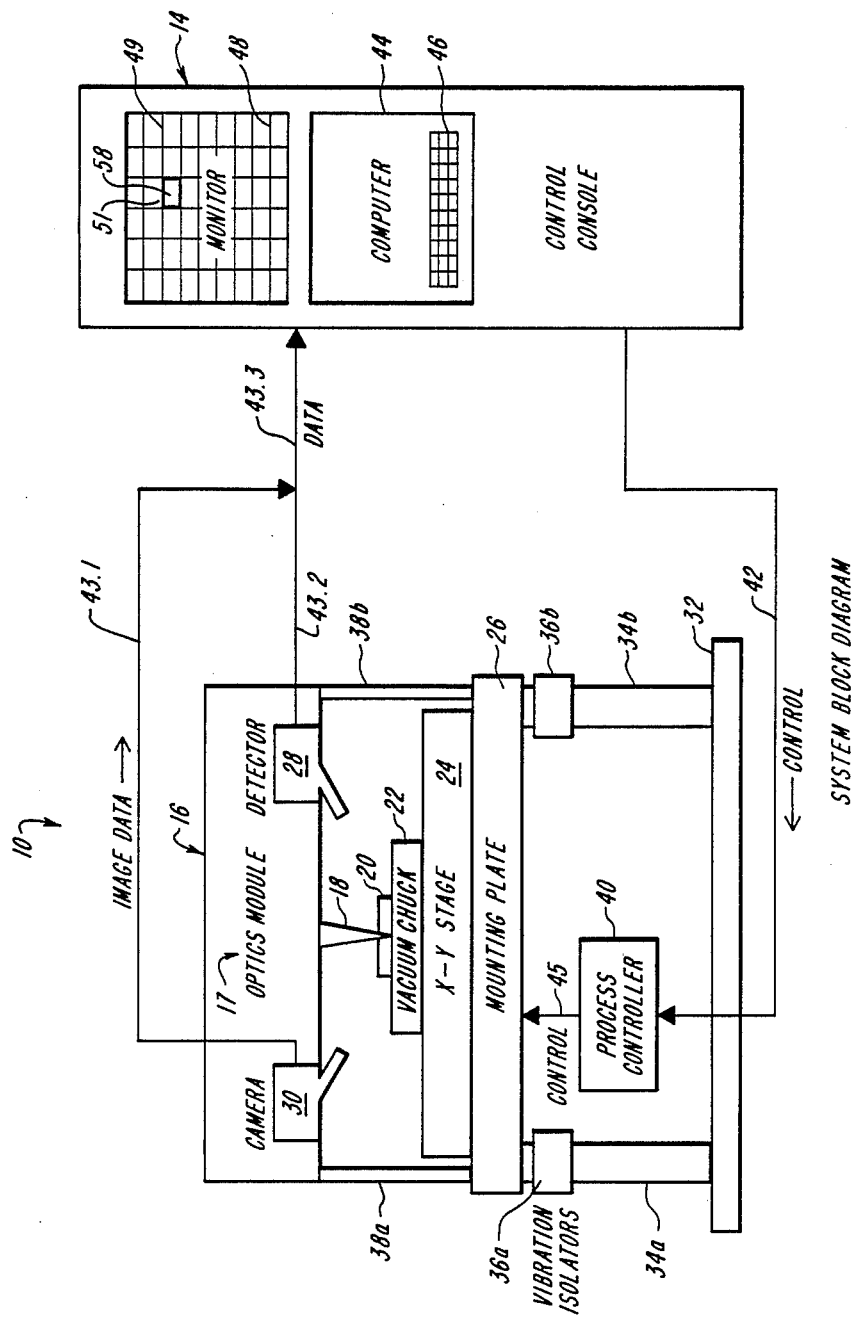
FIG. 1 depicts a defect detection and location system in accordance with the invention.

FIG. 1 depicts a system 10 constructed in accordance with the invention, for detecting and locating defects in an LCD panel. The system 10 generates an interrogating light beam 18 to scan a workpiece 20, detects reflected, refracted, scattered or transmitted light resulting from impingement of the beam 18 on the workpiece 20, and processes electrical signals representative of the resulting light to detect and locate defects on the workpiece 20. The system 10 thus optically examines a workpiece — such as an LCD panel — to detect defects in ordinarily regular lines or areas of reflective and non-reflective patterns.

The system 10 includes an inspection unit 16 and data processing and control unit 14. Inspection unit 16, comprising a light source module 17, detector 28 and camera 30, can be affixed by a plurality of support columns, exemplified by columns 38a and 38b, to a mounting plate 26. Mounting plate 26, in turn, can be coupled to a base 32 through a plurality of vibration isolators and support columns exemplified by isolators 36a, 36b, and columns 34a, 34b, respectively. Light source module 17 can incorporate conventional optical elements, typically including a laser, for generating an interrogating light beam 18 to impinge upon and scan the workpiece 20.

Scanning is effected by introducing relative motion between the workpiece 20 and beam 18, through actuating movement of either the workpiece 20 or beam 18. In the illustrated embodiment, an LCD panel, or other workpiece 20 to be inspected, is clamped by a mounting element, such as a conventional vacuum chuck 22, to retain the workpiece 20 in a selected initial position with respect to the light source module 17. The vacuum chuck 22 can be mounted on a conventional X-Y table or stage 24, which responds to applied control signals for moving the vacuum chuck 22 and workpiece 20 in a predetermined pattern with respect to the light source module 17. The illustrated X-Y stage 24 can actuate movement of the workpiece 20 in first and second orthogonal directions — "X" and "Y" — substantially perpendicular to the axis of propagation of the interrogating light beam 18. Alternatively, the optics module 17 can incorporate conventional beam steering elements for steering the interrogating light beam 18 in first and second orthogonal directions in a predetermined pattern about the workpiece 20.

A preferred embodiment of the invention employs co-deflection of both stage 24 and interrogating light beam 18. Thus, for example, in scanning an LCD panel having jagged arrays of LCD elements —as discussed hereinafter in connection with FIG. 3— stage 24 can be scanned linearly, while beam steering elements selectively deflect the interrogating light beam 18 to track non-linearities in the arrays of LCD elements.

When the interrogating light beam 18 scans the workpiece 20, the photodetector 28 detects reflected, refracted, scattered or transmitted light resulting from impingement of the light beam 18 upon the LCD panel. Photodetector 28 can be a conventional electro-optical device designed and constructed in accordance with known principles, and can include a photomultiplier or other conventional light-sensitive element for detecting light. The photodetector 28 responds to detected light in a known manner by generating a detector signal having an instantaneous value representative of the magnitude of the detected light. This detector signal can be transmitted by conductor 43.2 and bus 43.3 to processing module 14 for evaluation.

As indicated in FIG. 1, module 14 can contain a computer 44, monitor 48 and user input device 46. Computer 44 can include a microprocessor, workstation, logic gate array, or other analog or digital circuit or device, designed, implemented, constructed and programmed in accordance with conventional engineering practice, for processing data-representative signals under the control of predetermined program steps. Computer 44 reads the value of the detector signal asserted over bus 43.3, continuously evaluates the amplitude of the detector signal, and executes a known algorithm for detecting discontinuities in the magnitude of the detector signal. These discontinuities have been observed to be representative of physical defects in ordinarily regular lines or areas of reflective and non-reflective patterns on an LCD panel.

As a result of the scanning function discussed above, each instantaneous detector signal value generated by the detector 28 corresponds with a particular position of the beam 18 relative to the workpiece 20 ("beam/workpiece position"). In an embodiment of the invention, the instantaneous value of the detector signal generated by the photodetector 28 can be correlated with the beam/workpiece position, to permit determination of the location of detected defects. This correlation is executed by computer 44.

In particular, the X-Y stage 24 or beam-steering elements in optics module 17 can be controlled by signals asserted by computer 44, and computer 44 can monitor the value of these control signals to determine the instantaneous position of the interrogating light beam 18 with respect to the LCD panel 20. Alternatively, the X-Y stage 24 or beam-steering elements in optics module 17 can incorporate a conventional position signalling element for generating a position signal having an instantaneous value representative of beam/workpiece position. Based on the value of the control signals or position signals, computer 44 can correlate detected light amplitude with beam/workpiece position, and can therefore correlate each detected discontinuity in the value of the detector signal with a corresponding location on the LCD panel, to assign a location to each detected defect on the LCD panel.

As indicated in FIG. 1, a preferred embodiment of the invention includes imaging elements, exemplified by camera 30. The camera 30 can include conventional vidicon or CCD elements, and preferably includes optical microscope elements for generating a magnified the image of the LCD panel 20. Camera 30, in accordance with conventional practice, generates an image of the LCD panel 20 by collecting light reflected from the LCD panel 20, and generating image data signals representative of the LCD panel in response to the collected light. The image data signals generated by the camera 30 can be transmitted to the data processing module 14 over line 43.1 and bus 43.3, as illustrated in FIG. 1.

Computer 44 implements known techniques for processing the image data signals received over line 43.3, to generate monitor-driving image signals representative of the LCD panel. A monitor 48, in electrical communication with an output port of computer 44, displays an image 49 of the LCD panel in response to the monitor-driving image signals. Moreover, computer 44, in accordance with known computer graphics techniques, can highlight or otherwise indicate, in association with the image 49 displayed on the monitor 48, the location of a detected LCD defect 58. This highlighting can be effectuated, for example, by generating and displaying brackets 51 at a monitor screen location corresponding to that of the detected defect 58.

FIG. 1 further indicates that the invention can include a process controller 40, responsive to process control signals from computer 44, for controlling the scanning function. In particular, computer 44 can generate the process control signals in response to selected values of the position signals, and can assert control signals over line 42 to the process controller 40. In turn, the process controller 40 asserts control signals over line 45 to the X-Y stage 24 or beam-steering elements in optics module 17, to actuate and control the movement of the X-Y stage 24 or beam-steering elements in optics module 17. Process control can also be asserted by user input devices, such as keyboard 46 contained in control and processing module 14 of FIG. 1. Keyboard 46 receives user input and transmits user input signals to computer 44, which in turn generates process control signals in response to the received user input signals.

The system 10 can also include a workpiece transport device for automatic loading and unloading of LCD panels 20 or workpiece-holding cassettes on and off the vacuum chuck 22. The workpiece transport device can be actuated by transport control signals generated by computer 44.

Figure 2:
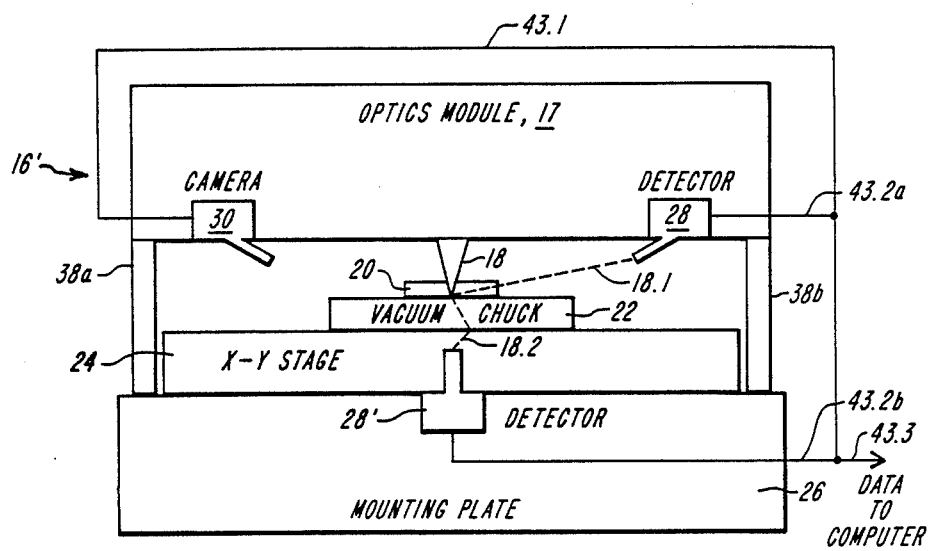
FIG. 2 depicts scanning and detection elements utilized in the embodiment of FIG. 1.

As depicted in FIG. 2, the inspection module 16' can include multiple photodetectors, each generating a respective stream of detector signals. In particular, as FIG. 2 indicates, at least a first photodetector 28 can be positioned to detect reflected light 18.1 resulting from reflection of the interrogating light beam 18 from the LCD panel 20. At least a second photodetector 28' can be positioned to detect transmitted, scattered or refracted light 18.2 resulting from impingement of the beam 18 upon the LCD panel 20. The detector signals generated by detectors 28 and 28' are transmitted to computer 44 over bus 43.3, and lines 43.2a and 43.2b, respectively. In accordance with this embodiment of the invention, computer 44 can compare detector signals generated by detector 28, representative of reflected light 18.1, and detector signals generated by detector 28', representative of transmitted, scattered or refracted light 18.2 to provide detection of defects in the LCD panel 20. Conventional signal thresholding and signal error correction techniques can be implemented in computer 44 for evaluating the detector signals, in accordance with known signal processing practice.

Figure 3:
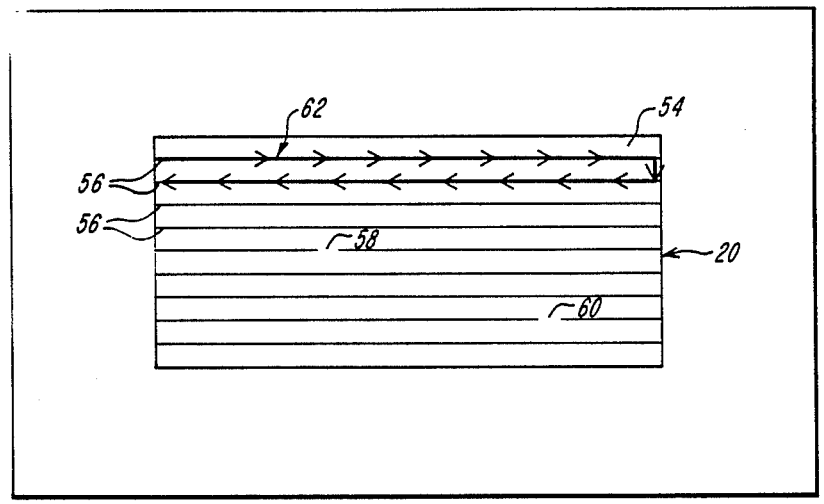
FIG. 3 depicts a scanning pattern utilized for inspection of an LCD panel in accordance with the invention.

As illustrated in FIG. 3, in one practice of the invention, a raster scan path 62 can be implemented to inspect the arrays 56 characteristic of the surface 54 of an LCD panel 20, to detect physical discontinuities 58 and 60. While FIG. 3 illustrates an LCD panel having linear arrays of LCD elements, the invention can be employed for scanning and defect detection in LCD panels having jagged or otherwise non-linear arrays of LCD elements. This scanning pattern is implemented by computer 44 (FIG. 1), which generates process control signals for actuating the X-Y stage 24, or beam-steering elements in optics module 17, for scanning the interrogating light beam 18 along a raster path 62 defined by arrays 56 of LCD elements on the LCD panel 20. In an embodiment utilizing co-deflect of stage 24 and interrogating light beam 18, stage 24 can be scanned linearly, while beam steering elements selectively deflect the interrogating light beam 18 to track non-linearities in the arrays of LCD elements.

Computer 44 can also be programmed in accordance with known techniques to actuate initial scanning along the arrays 56 of the LCD panel 20 to accumulate a knowledge base corresponding to features of the LCD panel, and subsequent scanning of the LCD panel 20 to detect defects in the LCD panel. In particular, during the initial scan, computer 44 can utilize beam/workpiece position data and detector signal data to accumulate a knowledge base, and can subsequently apply known image processing techniques to detector signal data, for detection of defects. While the invention is advantageously practiced in connection with detection of breaks or discontinuities in linear or jagged LCD arrays, the invention can also be utilized for inspecting inter-line areas on an LCD or other workpiece for other types of defects.

It will thus be seen that the invention efficiently attains the objects set forth above, among those made apparent from the preceding description. In particular, the invention provides accurate real-time detection and location of defects in LCD arrays.

It will be understood that changes may be made in the above construction and in the foregoing sequences of operation without departing from the scope of the invention. It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

Having described the invention, what is claimed as new and secured by Letters Patent is:

1. Apparatus for locating defects in a substantially planar liquid crystal display (LCD) panel, the apparatus comprising light source means for generating an interrogating light beam to impinge upon the LCD panel, scanning means for introducing relative motion between said interrogating light beam and the LCD panel to scan said interrogating light beam in a predetermined pattern about the LCD panel, position signalling means for generating a position signal having an instantaneous value representative of an instantaneous position of said interrogating light beam with respect to the LCD panel, photodetector means for detecting any of reflected, refracted, scattered or transmitted light resulting from impingement of said interrogating light beam upon the LCD panel, and generating in response thereto a detector signal having an instantaneous value representative of detected magnitude of said reflected, refracted, scattered or transmitted light, each said instantaneous detector signal value corresponding with the instantaneous position of said interrogating light beam with respect to the LCD panel, and discontinuity detection means, responsive to said detector signal, for detecting discontinuities in the value of said detector signal, said discontinuities being representative of defects in the LCD panel, said discontinuity detection means including location means, responsive to said detector signal and said position signal, for correlating each said discontinuity in the value of said detector signal with a corresponding location on the LCD panel to assign a location to each detected defect on the LCD panel.

2. Apparatus according to claim 1, wherein said light source means includes a laser.

3. Apparatus according to claim 1, further comprising mounting means for maintaining the LCD panel in a selected position with respect to said light source means.

4. Apparatus according to claim 3, wherein said mounting means includes vacuum chuck means for retaining the LCD panel in contact with the mounting means by action of vacuum force.

5. Apparatus according to claim 3, wherein said scanning means includes actuator means for moving said mounting means with respect to said light source means in a predetermined pattern.

6. Apparatus according to claim 5, wherein said actuator means includes X-Y stage means for moving said mounting means in at least first and second orthogonal directions substantially perpendicular to a direction of propagation of said interrogating light beam.

7. Apparatus according to claim 1, wherein said scanning means includes beam steering means for steering said interrogating light beam in a predetermined pattern.

8. Apparatus according to claim 7, wherein said beam steering means includes means for steering said interrogating light beam in at least first and second orthogonal directions.

9. Apparatus according to claim 1, wherein said discontinuity detection means includes digital processing means for processing digital data-representative signals in accordance with predetermined program steps.

10. Apparatus according to claim 1, wherein said discontinuity detection means includes means for detecting physical discontinuities in an array of LCD elements.

11. Apparatus according to claim 9, further comprising imaging means, in electrical communication with said digital processing means, for generating image data signals corresponding to an image of the LCD panel.

12. Apparatus according to claim 11, wherein said imaging means includes at least a first camera means for collecting light reflected from the LCD panel and generating said image data signals in response to said collected light.

13. Apparatus according to claim 11,
wherein said digital processing means includes means for processing said image data signals to generate displayable image signals representative of the LCD panel, and
further comprising monitor means, in electrical communication with said digital processing means, for displaying an image of the LCD panel in response to said displayable image signals.

14. Apparatus according to claim 13, wherein said digital processing means further includes means for indicating, in association with the image displayed on said monitor means, the location of a detected defect on the LCD panel.

15. Apparatus according to claim 9,
further including process control means, responsive to process control signals, for controlling at least said scanning means, and
wherein said digital processing means includes means for generating said process control signals in response to said position signals and said predetermined program steps.

16. Apparatus according to claim 15,
further comprising user input means, in communication with said digital processing means, for
receiving user input and
transmitting to said digital processing means, in response to said user input, a set of user input signals representative of said user input, and
wherein said digital processing means includes means for generating said process control signals in response to said user input signals.

17. Apparatus according to claim 1, wherein
said photodetector means includes at least first and second photodetectors for generating at least first and second detector signals, respectively,
said first photodetector being positioned to detect reflected light resulting from impingement of said interrogating light beam upon the LCD panel, said first detector signal being representative of detected reflected light, and
said second photodetector being positioned to detect any of transmitted, scattered or refracted light resulting from impingement of said interrogating light beam upon the LCD panel, said second detector signal being representative of detected transmitted or refracted light.

18. Apparatus according to claim 17, wherein said discontinuity detection means includes means for
evaluating said first detector signals during selected first scanning periods, and
evaluating said second detector signals during selected second scanning periods.

19. Apparatus according to claim 17, wherein said discontinuity detection means includes means for comparing said first and second detector signals, to provide detection of defects in the LCD panel.

20. Apparatus according to claim 9, further comprising
mounting means for maintaining the LCD panel in a selected position with respect to said light source means, and
transport means for automatic loading and unloading of LCD panels on and off said mounting means, said transport means being responsive to transport control signals, and
wherein said digital processing means includes means for generating said transport control signals in response to said predetermined program steps.

21. Apparatus according to claim 9, wherein said digital processing means includes
means for generating said process control signals to enable said scanning means to cause said interrogating light beam to scan along selected paths defined by arrays of LCD elements on the LCD panel.

22. Apparatus according to claim 21, wherein said digital processing means includes means for generating said process control signals to enable said scanning means to
first scan along said paths to accumulate a knowledge base corresponding to features of the LCD panel, and
subsequently scan said LCD panel to detect defects in the LCD panel.

* * * * *